US011767613B2

(12) United States Patent
Miedema et al.

(10) Patent No.: US 11,767,613 B2
(45) Date of Patent: Sep. 26, 2023

(54) MEDICAL IMPLANT PREFORM PRODUCED USING AN INSIDE OUT FLIPPING METHOD

(71) Applicant: Xeltis AG, Zurich (CH)

(72) Inventors: Jurgen Sander Miedema, Eindhoven (NL); Martijn Antonius Johannes Cox, Budel (NL); Christophe Pierre Edouard Naz, Fontainebleau (FR)

(73) Assignee: Xeltis AG, Zurich (CH)

( * ) Notice: Subject to any disclaimer, the term of this patent is extended or adjusted under 35 U.S.C. 154(b) by 124 days.

(21) Appl. No.: 16/954,688

(22) PCT Filed: Dec. 20, 2018

(86) PCT No.: PCT/EP2018/086166
§ 371 (c)(1),
(2) Date: Jun. 17, 2020

(87) PCT Pub. No.: WO2019/129636
PCT Pub. Date: Jul. 4, 2019

(65) Prior Publication Data
US 2021/0087710 A1    Mar. 25, 2021

Related U.S. Application Data

(60) Provisional application No. 62/610,987, filed on Dec. 28, 2017.

(51) Int. Cl.
*B29D 23/00* (2006.01)
*D01D 5/00* (2006.01)
(Continued)

(52) U.S. Cl.
CPC ........... *D01D 5/003* (2013.01); *A61F 2/2415* (2013.01); *B29B 11/10* (2013.01); *B29D 23/00* (2013.01);
(Continued)

(58) Field of Classification Search
CPC ...... B29D 23/00; B29B 11/10; D01D 5/0076; D01D 5/0007; D01D 5/003; A61F 2/2412; A61F 2/2415; A61F 2240/001
See application file for complete search history.

(56) References Cited

U.S. PATENT DOCUMENTS

2014/0086971 A1\* 3/2014 Hall ..................... A61L 29/16
514/56

FOREIGN PATENT DOCUMENTS

| WO | WO2014/163795 | \* 10/2014 | ............ A61L 27/56 |
| WO | WO2016138416 | 9/2016 | |
| WO | WO2017047902 | 3/2017 | |

\* cited by examiner

*Primary Examiner* — Monica A Huson
(74) *Attorney, Agent, or Firm* — LUMEN PATENT FIRM

(57) ABSTRACT

A method of making a medical implant is provided by electrospinning a polymer solution to form a preform around a mandrel. The formed preform distinguishes an inner surface and an outer surface. The formed preform is removed from the mandrel and flipped inside-out resulting in the inner surface of the formed preform becoming the outer surface of the inside-out flipped preform, and the outer surface of the formed preform becoming the inner surface of the inside-out flipped preform. At least part of the inside-out flipped preform forms the medical implant such as e.g. an artificial heart valve, an artificial leaflet, an artificial graft, or an artificial vessel. The products made according to the method of this invention greatly improve the performance and durability of the medical implant.

3 Claims, 15 Drawing Sheets

(51) Int. Cl.
 *A61F 2/24* (2006.01)
 *B29B 11/10* (2006.01)
(52) U.S. Cl.
 CPC ...... *D01D 5/0076* (2013.01); *A61F 2240/001* (2013.01)

Two lobes

Four lobes

Five lobes

MEDICAL IMPLANT PREFORM PRODUCED USING AN INSIDE OUT FLIPPING METHOD

CROSS-REFERENCE TO RELATED APPLICATIONS

This application is a 371 of PCT application PCT/EP2018/086166 filed Dec. 20, 2018. PCT application PCT/EP2018/086166 claims the benefit of U.S. Provisional application 62/610,987 filed Dec. 28, 2017.

FIELD OF THE INVENTION

The invention relates to electro-spinning of complex shapes using an inside out flipping technique to create medical implant preforms.

BACKGROUND OF THE INVENTION

An artificial heart valve is a device implanted in the heart of a patient with valvular heart disease. When one of the four heart valves malfunctions, the medical choice may be to replace the natural valve with an artificial valve. In one example, a cylindrical preform is used to create a heart valve. Due to the normal fiber alignment of the preform, the created heart valve will naturally be in an open position (FIG. 1A). Preferably, however, the heart valve would naturally be in a closed position, which is advantageous in the performance of the heart valve (FIG. 1B). As the heart valve is more prone to close, the closing volume and therefore the regurgitant fraction are reduced. Another advantage is that the normally closed position reduces strains occurring during diastole (i.e. the closed phase). The pressure differential over the heart valve during diastole, creates a strain in the leaflet material. In a heart valve that is normally open, the leaflets have already undergone a large deformation to reach the closed position and are then loaded by the pressure differential. In a normally closed heart valve, the leaflets are subjected to a small deformation before reaching the fully closed position. As the deformation is decreased, the occurring stresses will subsequently be smaller.

Using several conventional techniques, it is possible to create a normally closed valve. By means of special suture techniques, it is possible to pull the leaflets into a closed position. Alternatively, it is possible to anneal the leaflet material in a closed position. Both of these techniques have no effect on the material distribution within the leaflet. While these conventional techniques may help to improve the performance of the valve, they will do nothing to decrease the stresses that occur in the leaflet during diastole. The present invention addresses at least some of these concerns by providing a method to produce the complex shapes that would improve the performance and durability of a heart valve.

Electrospinning is a fiber production method which uses electric force to draw charged threads of polymer solutions or polymer melts up to fiber diameters in the order of some hundred nanometers. The electric charge creates the force by which the fiber jet is attracted to the target. To achieve a uniform distribution of fibers upon the target, the electric field has to be as uniform as possible. A perfect cylinder theoretically creates a uniform electric field in electrospinning. Any deviation from this cylinder creates charge concentrations. Any charge concentration creates a variation in the distribution of fibers upon the target.

The geometry of the electrospinning target can be optimized to reduce any charge concentrations. Generally speaking, charge concentrations can be reduced by keeping the inner diameter, outer diameter and the lobe diameter as close as possible to each other (FIGS. 2A-B). Changing any one of these diameters caused for a less uniform charge distribution.

FIGS. 3A-C show a number of geometries with an approximation of the resulting fiber layer that can be spun upon the mandrels. From left to right in FIGS. 3A-C, these targets have a less uniform charge distribution. A less uniform charge distribution results in having a less uniform fiber distribution. In some cases, this might result in bridging, as shown on the far right. In this case the fibers are not deposited on the concave surface anymore. For various applications, however, it is highly desirable to produce preforms that not only have different complex geometries, but also have a uniform thickness distribution within these preforms. The present invention addresses at least some of these concerns by providing a method to produce the complex geometries that would improve the performance and durability of a medical implant such as valves.

SUMMARY OF THE INVENTION

The present invention is a method, a product made by the method and uses/applications of the method and products of medical implants. In one embodiment a method of making a medical implant distinguishes using a polymer solution to form (e.g. by electrospinning) a preform with a desired thickness around the surface of a mandrel. The formed preform distinguishes an inner surface and an outer surface. The formed preform is removed from the mandrel and flipped inside-out resulting in the inner surface of the formed preform becoming the outer surface of the inside-out flipped preform, and the outer surface of the formed preform becoming the inner surface of the inside-out flipped preform. At least part of the inside-out flipped preform forms the medical implant. In another embodiment the invention is a product, e.g. a medical implant made by the method or more specifically an artificial heart valve, an artificial leaflet, an artificial graft, or an artificial vessel. In yet another embodiment the invention is a use or application of the made product.

In a specific example, the mandrel distinguishes at least one convex area. As such the inside-out flipped preform distinguishes at least one concave area reflecting the inverse of the at least one convex area of the mandrel. More generally speaking in yet another example, the mandrel distinguishes at least one three-dimensional shaped area. As such the inside-out flipped preform distinguishes at least one three-dimensional shaped area reflecting the inverse shaped area of the at least one three-dimensional shaped area of the mandrel. In still another example, the mandrel is tubular with at least one three-dimensional shaped area. As such the inside-out flipped preform is tubular with at least one three-dimensional shaped area reflecting the inverse three-dimensional shaped area of the shaped area of the mandrel. In yet another example, the mandrel is cylindrical and the inside-out flipped preform is cylindrical. In still another example, the mandrel is tubular and the inside-out flipped preform is tubular. The products made according to the method of this invention greatly improve the performance and durability of a medical implant.

BRIEF DESCRIPTION OF THE DRAWINGS

FIG. 6B (right) shows the fiber distribution thickness of the cross-section of the preform. This illustrates limitations known in the art on electrospinning of too concave surfaces, namely fiber bridging and thickness gradients.

FIG. 7B (right) shows the preform once the preform shown in FIG. 7B (left) is flipped inside out. FIG. 7C (right) shows the fiber distribution thickness of the cross-section of the flipped preform (FIG. 7C (left). This way flipping inside out overcomes the problem of bridging, by avoiding spinning on a too concave surface.

FIG. 8B (right) shows the preform once the preform shown in FIG. 8B (left) is flipped inside out. This illustrates that the circumferential profile can be varied along the length of the mandrel and the resulting preform.

FIG. 9B (right) shows the preform once the preform shown in FIG. 9B (left) is flipped inside out.

FIG. 10B (right) shows the preform once the preform shown in FIG. 10B (left) is flipped inside out. FIG. 10C shows a cross-section view before flipping (left) and after flipping (right).

FIG. 11B (right) shows the preform once the preform shown in FIG. 11B (left) is flipped inside out. FIG. 11C shows a cross-section view before flipping (left) and after flipping (right).

FIG. 12B (right) shows the preform once the preform shown in FIG. 12B (left) is flipped inside out. FIG. 12C shows a cross-section view before flipping (left) and after flipping (right).

DETAILED DESCRIPTION

Fiber Alignment

In one embodiment, the present invention is a method of producing a preform that enables creating a normally closed valve (e.g. heart valve) using a cylindrical mandrel. First, a cylindrical preform of a desired diameter is produced on a cylindrical mandrel for example by electrospinning Second, the formed preform is then turned inside out, by flipping the preform inside out, once the preform is removed from the mandrel. This will then result in having a preform with its original inner surface now on the outside. This method does not require any further post-processing steps, such as annealing or a dedicated suture technique as will be explained below.

Preferential Inwards Bending

Figure 1A:
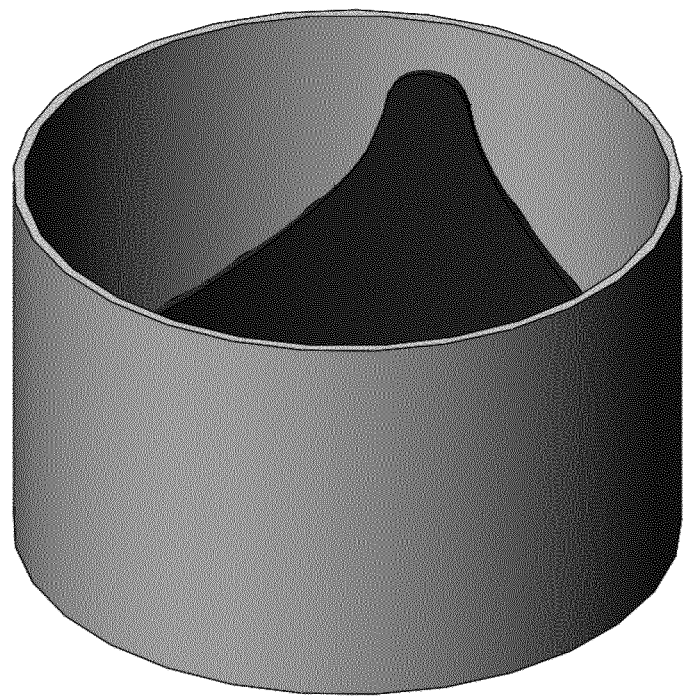
FIGS. 1A-B show according to an exemplary embodiment of the invention a normally open valve (FIG. 1A) and a normally closed valve (FIG. 1B). In this exemplary embodiment a trileaflet heart valve is formed by folding a tubular shape around a support frame with 3 upward posts.
Figure 1B:
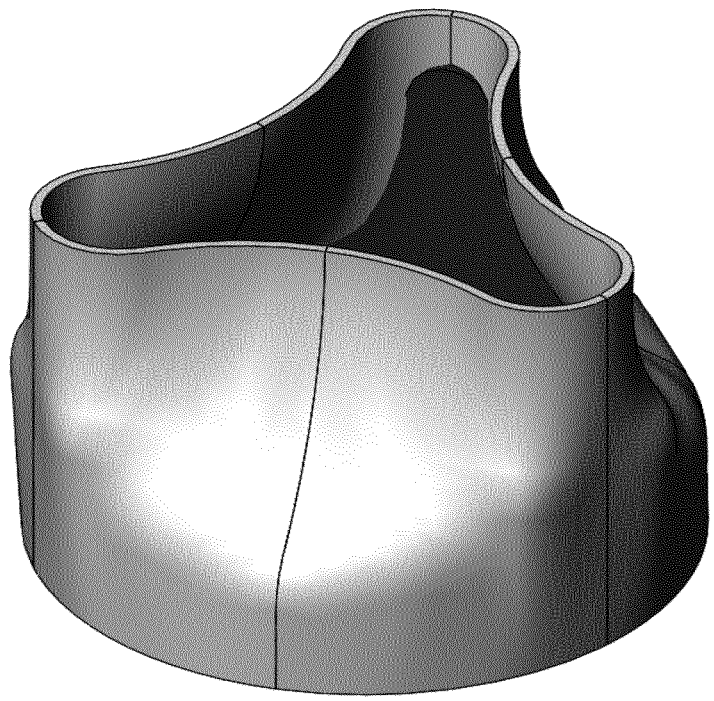
Figure 2A:
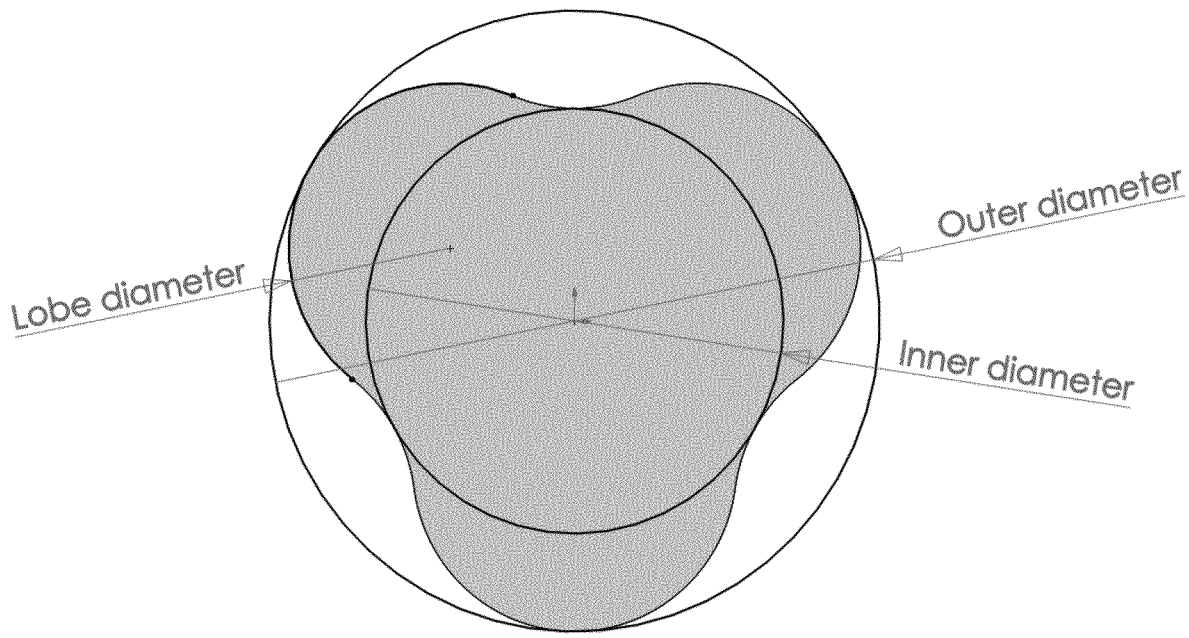
FIGS. 2A-B show according to an exemplary embodiment of the invention a definition of lobe diameter and/or inner diameter compared to outer diameter.
Figure 2B:
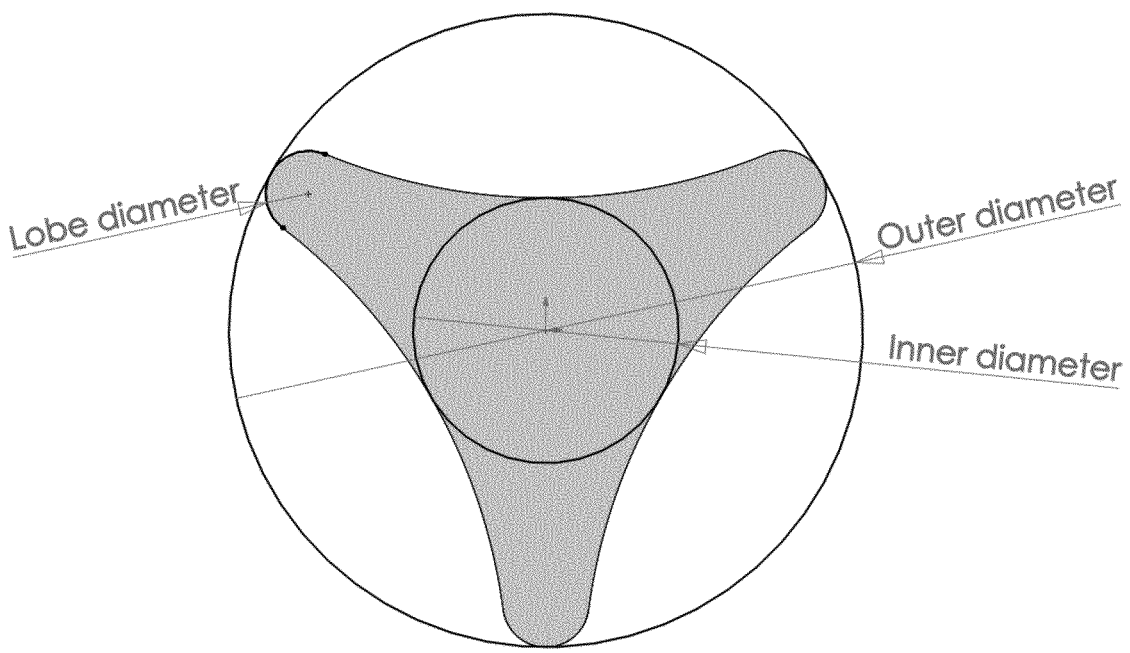
Figures 3A, 3B, 3C:
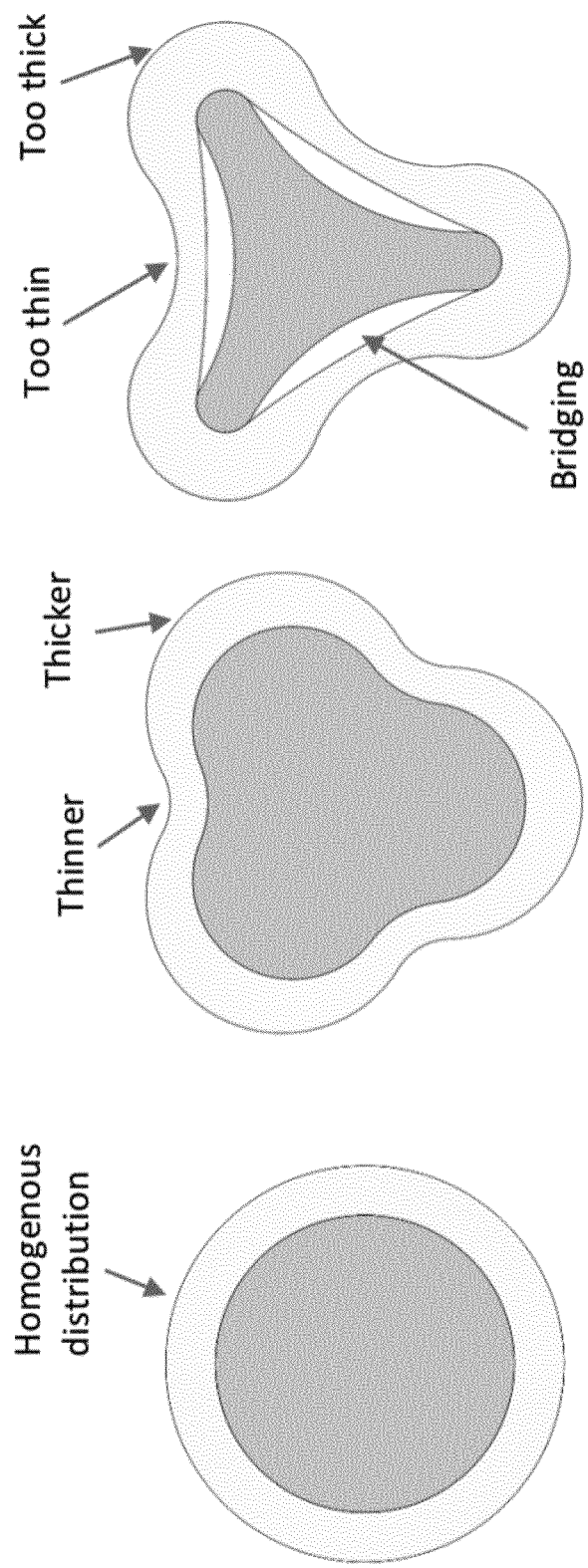
FIGS. 3A-C show that reducing lobe diameter and/or inner diameter compared to outer diameter (as defined in FIGS. 2A-B), results in a thickness gradient along the circumference of the electrospun structure (FIG. 3A). If lobe diameter and/or inner diameter are further reduced compared to outer diameter, the mandrel shape becomes too concave, resulting in fiber bridging (FIG. 3C). These phenomena are known in the art as limitations of the electrospinning process.
Figure 4B:
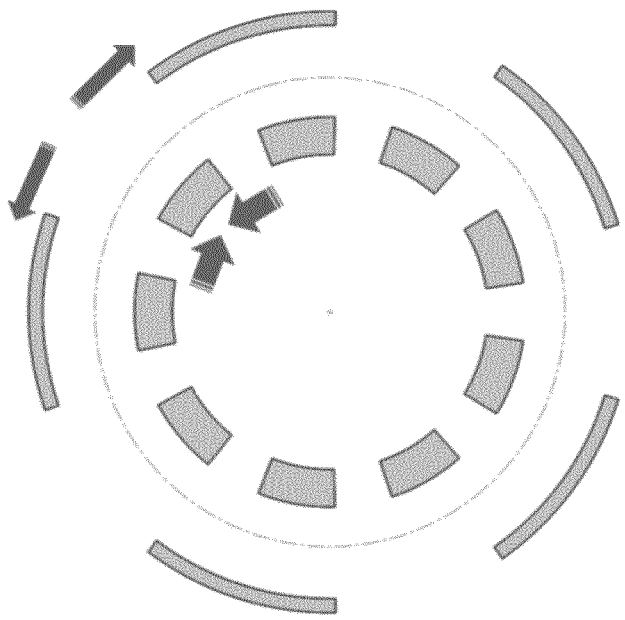
FIGS. 4A-B show according to an exemplary embodiment of the invention material distribution before (FIG. 4A) and after flipping inside out (FIG. 4B). Arrows in FIG. 4B indicate compression forces at the inner surface and stretch forces at the out surface. As a result of these forces, the material will have the tendency to bend inward after flipping inside out, which can be beneficial for example when creating a heart valve with a preference for the closed position.
Figure 4A:
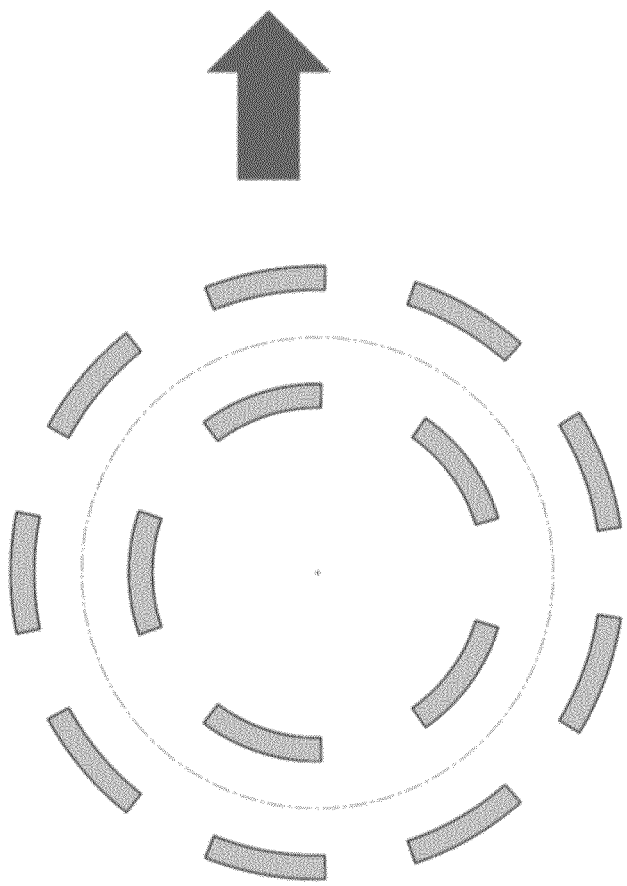

The method of flipping inside-out a formed preform changes the distribution of the material within the preform, which creates forces within the preform (FIGS. 4A-B). The inside surface (which after flipping has become the outer surface) is stretched to conform to the desired outer diameter of the preform, while the outside surface (which after flipping has become the inner surface) is compressed to conform to the inner diameter of the preform. These forces combine to create a bending moment. Due to this bending moment, the preform preferentially bends inwards.

The occurring strains are dependent on the ratio between the inner and the outer diameter of the preform. The actual forces that occur are a function of the Young's modulus and the occurring strains.

The inner and outer strain $\varepsilon_i$ and $\varepsilon_o$ respectively, can be defined as a function of the inner and outer radii $R_i$ and $R_o$ by defining the change in circumferential length resulting from flipping inside out.

$$\varepsilon_i = \frac{2\pi R_o - 2\pi R_i}{2\pi R_o} = 1 - \frac{R_i}{R_o}$$

$$\varepsilon_o = \frac{2\pi R_i - 2\pi R_o}{2\pi R_i} = 1 - \frac{R_o}{R_i}$$

As an example, for a tube with an inner diameter $R_i$ of 10 mm and a wall thickness of 1 mm, the other diameter $R_o$ is 11 mm. After flipping inside out the inner layer (now outer layer) feels a residual tensile strain of ~9%, while the outer layer (now inner layer) feels a residual compressive strain of 10%. This creates an inward bending momentum in the material, which in one of the exemplary embodiments results in a heart valve scaffold with a tendency towards the closed position.

Reduction in Local Strains

For a valve made from a cylindrical preform, the preform undergoes a relatively large deformation when closing.

Figures 5A, 5B:
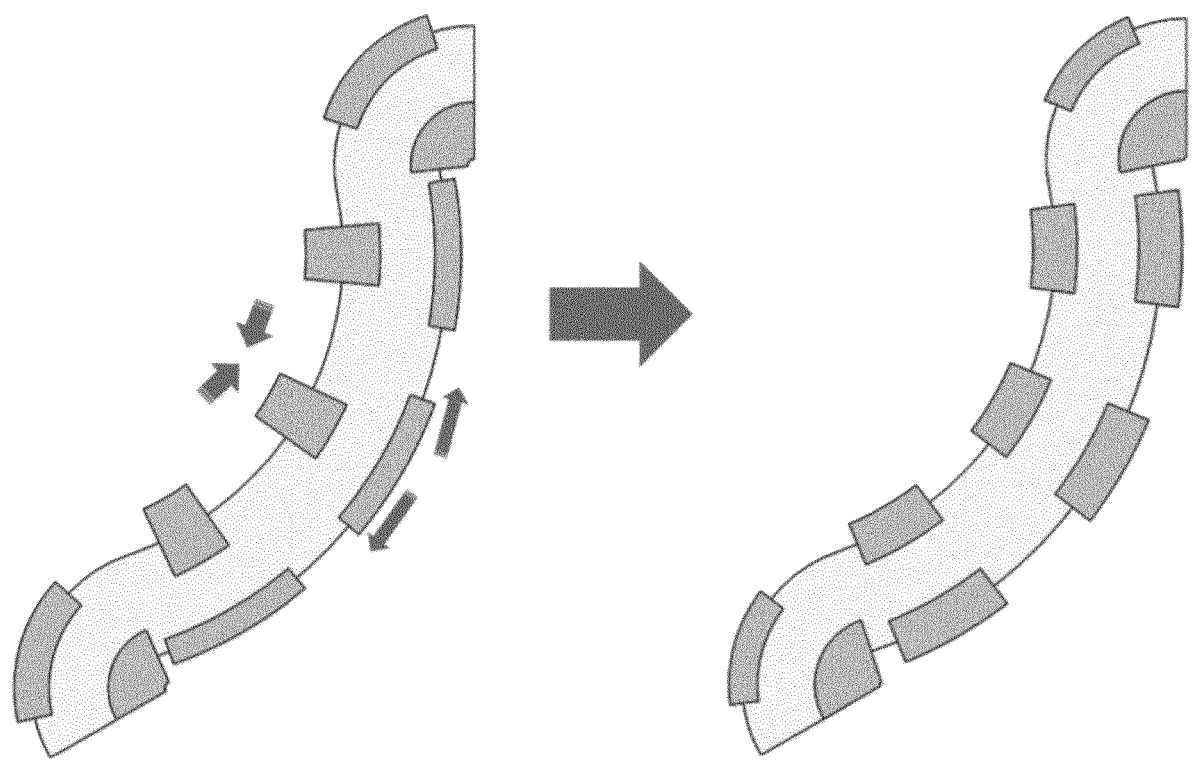
FIGS. 5A-B show according to an exemplary embodiment of the invention material distribution in a closed leaflet before (FIG. 5A) and after flipping inside out (FIG. 5B). Arrows indicate compression forces at the inner surface and stretch forces at the out surface. This indicates that a tubular preform that is flipped inside out has the tendency towards a closed valve configuration, compared to a tendency towards the open configuration for a tubular preform that is not flipped inside out.

These large deformations in the belly area of the leaflet create large strains in the material. In case of the inside-out preform, the deformations in the closed position are significantly reduced (FIGS. 5A-B). The neutral position of the preform is much more similar to the closed position, compared to the preform without flipping inside out. The highest loads are applied to a heart valve in its closed position. By reducing the strains in the closed position, the durability of the leaflet is increased. FIG. 5B shows a one-third section of a cylindrical preform that forms one leaflet of a heart valve. Arrows in FIG. 5B indicate compression forces at the inner surface and stretch forces at the outer surface.

Concave Geometries

In another embodiment, the present invention is a method of electro-spinning of a desired shape for a preform on a mandrel whereby the mandrel has the opposite or inverse shape of the finally desired shape of the preform.

First, a preform of a desired diameter is produced on the mandrel using electro-spinning Second, the formed preform is then turned inside out, by flipping the preform inside out, once the preform is removed from the mandrel. This will then result in having a preform with its original inner surface now on the outside, and the mandrel shape reversed/flipped as well. This method does not require any further post-processing steps, such as annealing or a dedicated suture technique as will be explained below. Furthermore, this process allows the manufacturing of complex shapes via electro-spinning, which would be challenging by definition with processes known in the art without any compromise neither on product quality nor on electro-spinning process.

In particular, electrospinning of a preform that has at least one area with a concave shape is performed on a mandrel that has the inverse shape with the corresponding convex shape area. The method according to this invention allows the manufacturing of such complex shapes with at least one concave area via electro-spinning with very limited compromise on the product quality.

Within the method of this invention conventional spinning methods can be used and microstructures can still be created as well.

As a person skilled in the art would appreciate, the method of this invention could be applied to various applications and various types of complex shapes as long as the mandrel can provide the mirror image of the desired shape of the preform. Generally speaking a three-dimensionally shaped area desired in a preform is established by using a mandrel having the inverse of that three-dimensionally shaped area and once the preform is created on that mandrel and then flipped inside out the desired preform with the three-dimensionally shaped area is then created. One example according to the method is the production of artificial heart valves. Another example according to the method is the production of artificial grafts or vessels.

Example 1

State-of-Art

Figure 6A:
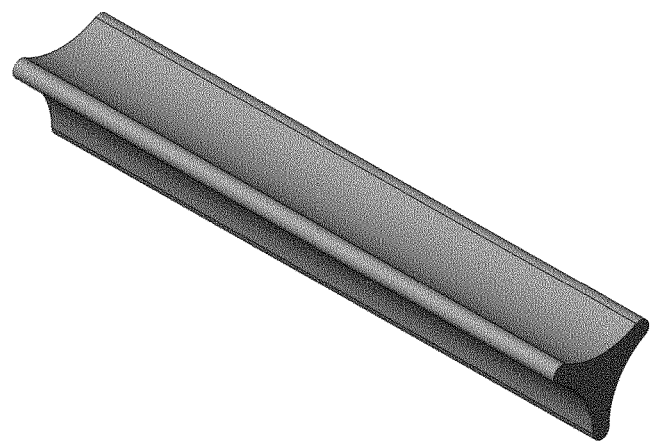
FIGS. 6A-B show according to a prior art example in FIG. 6A a mandrel which is used to create the preform shown in FIG. 6B (left).
Figure 6B:
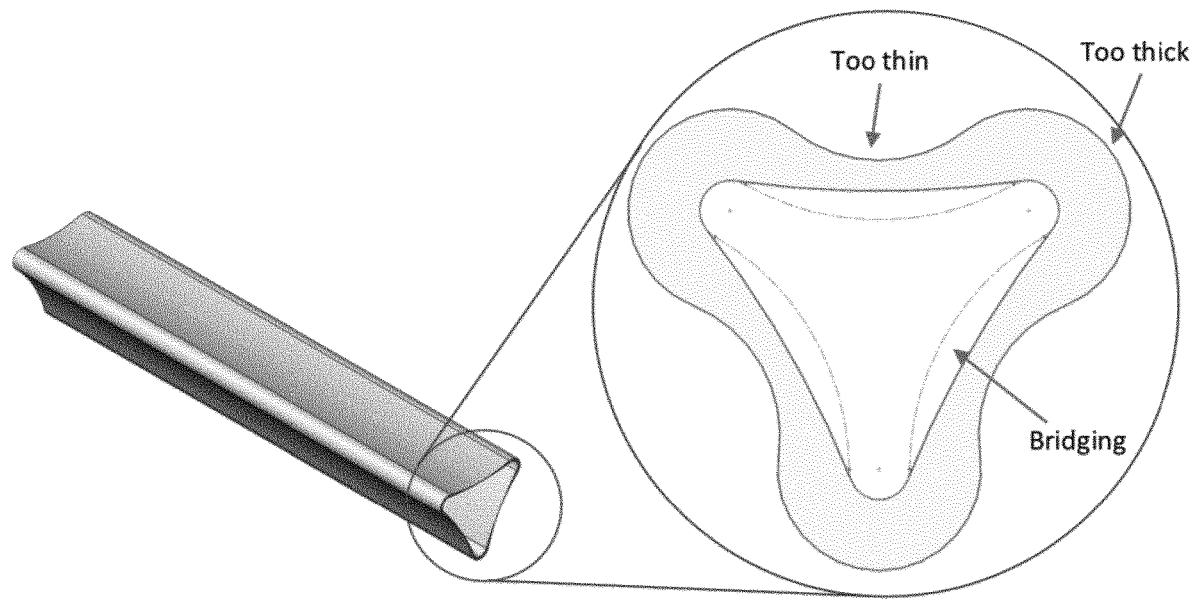

A preform with a geometry that distinguishes a number of concave surfaces is desired. In a state-of-art example the outer geometry of the mandrel (FIG. 6A) would match the desired inside geometry of the preform. A preform produced on this mandrel would exhibit a number of problems associated with electrospinning on complex geometries. Spinning on this mandrel would yield a preform similar to be one as shown in FIG. 6B (left). The preform would have a varying thickness distribution and show areas with bridging, where the preform will no longer be attached to the mandrel (FIG. 6B, right).

Flipping Inside Out

Figure 7A:
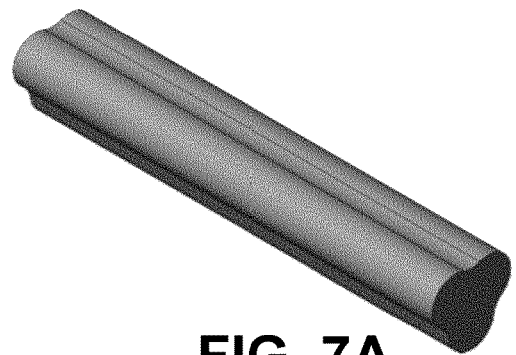
FIGS. 7A-C show according to an exemplary embodiment of the invention in FIG. 7A a mandrel which is used to create the preform shown in FIG. 7B (left).

To produce the same desired preform using the method of this invention, a mandrel with the inverse geometry is used (FIG. 7A). The mandrel distinguishes essentially convex surfaces, resulting in significantly less problems during the electrospinning process; a complex shape with mainly convex shapes and only very limited concave areas. In this embodiment, the target is uniformly formed along the whole length.

Figure 7B:
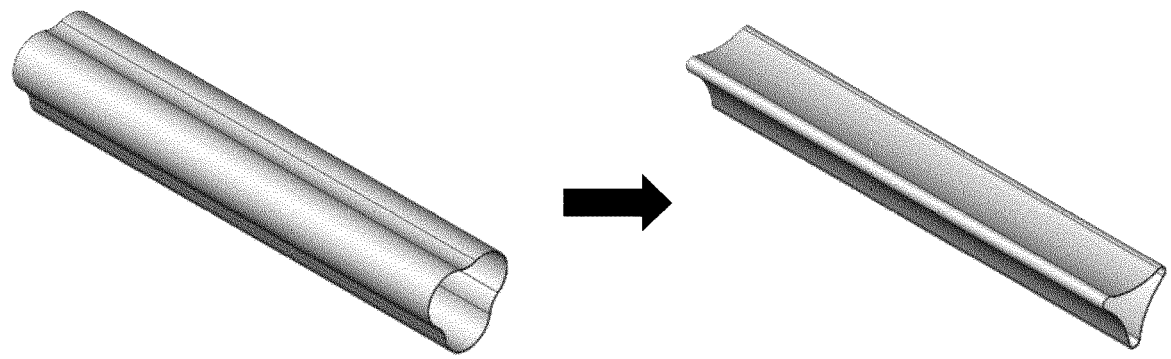
Figure 7C:
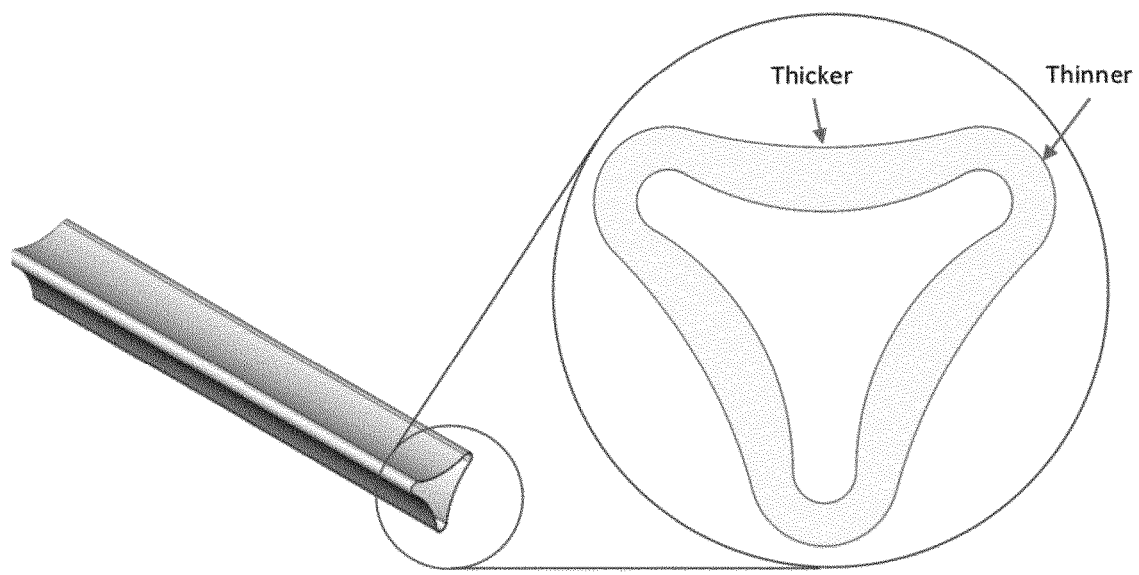

The three leaflets are produced by electro-spinning on this specially formed target mandrel (FIG. 7A). Subsequently the produced tubular preform (FIG. 7B, left) having convex extension areas is carefully flipped inside-out (FIG. 7B, right). This results in a complementary "tubular preform having concave extension areas (FIG. 7B, right). The resulting preform will exhibit a much more uniform thickness distribution as shown in FIG. 7C compared to the preform produces according to the state of art example as shown in FIGS. 6A-B.

Finally, the concave shape having three leaflets can for example be fixed or sutured to a covered frame. As an advantage the final tube area to be used for the design of the leaflets can be cut at any place since there is no difference along the length of the mandrel. In addition, several leaflets can be produced in one electrospinning step on the mandrel next to each other.

Example 2

Figure 8A:
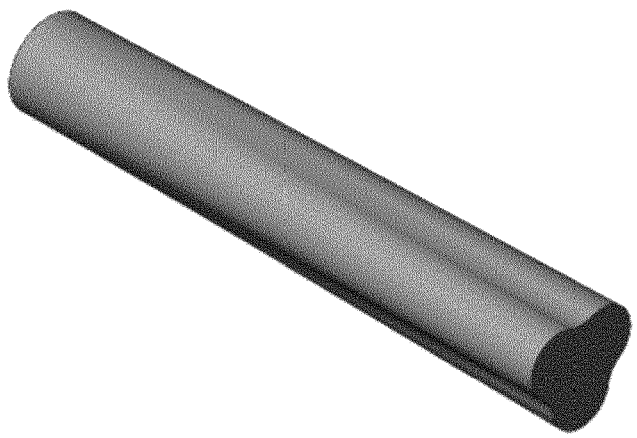
FIGS. 8A-B show according to an exemplary embodiment of the invention in FIG. 8A a mandrel which is used to create the preform shown in FIG. 8B (left).
Figure 8B:
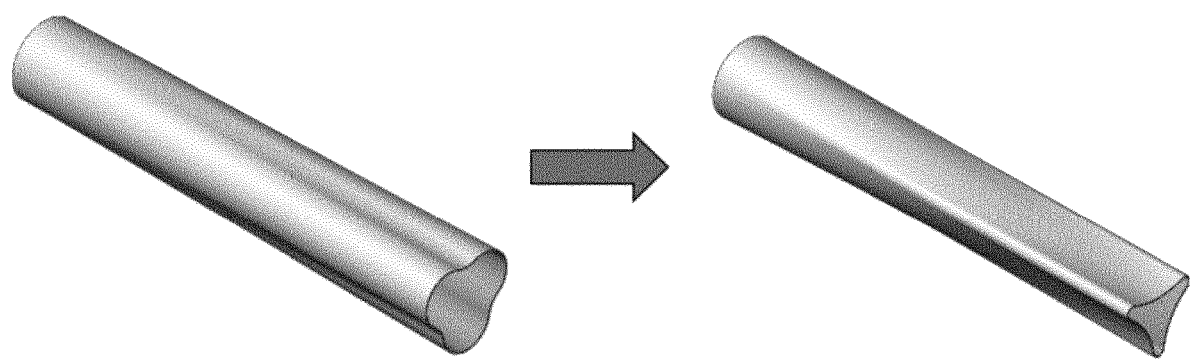

In the example of FIGS. 8A-B, the mandrel shown in FIG. 8A distinguishes a complex shape with mainly convex shapes and only very limited concave areas. In this example the mandrel and resulting preform are not uniformly formed along the whole length as shown, but shows a variation of the shape along its axis. FIG. 8B (left) is the preform that is formed using the mandrel (FIG. 8A). FIG. 8B (right) is the preform after the preform in FIG. 8B (left) is flipped inside-out. These tubular preforms could be advantageous in cases where the second end should stay open, e.g. for the production of transcatheter valves.

Example 3

Figure 9A:
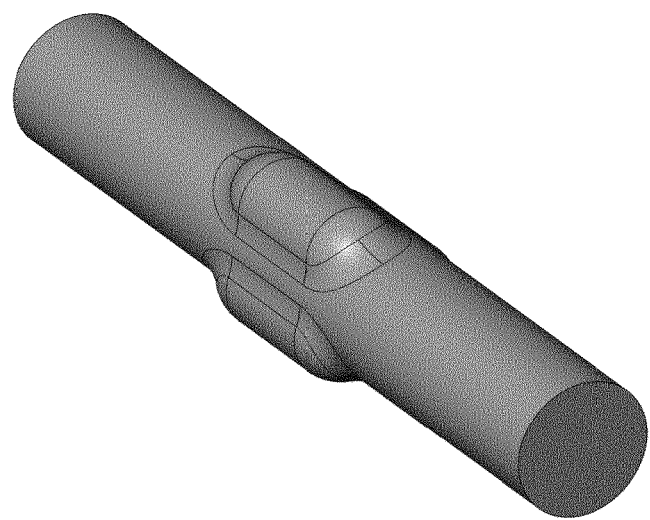
FIGS. 9A-B show according to an exemplary embodiment of the invention in FIG. 9A a mandrel which is used to create the preform shown in FIG. 9B (left).
Figure 9B:
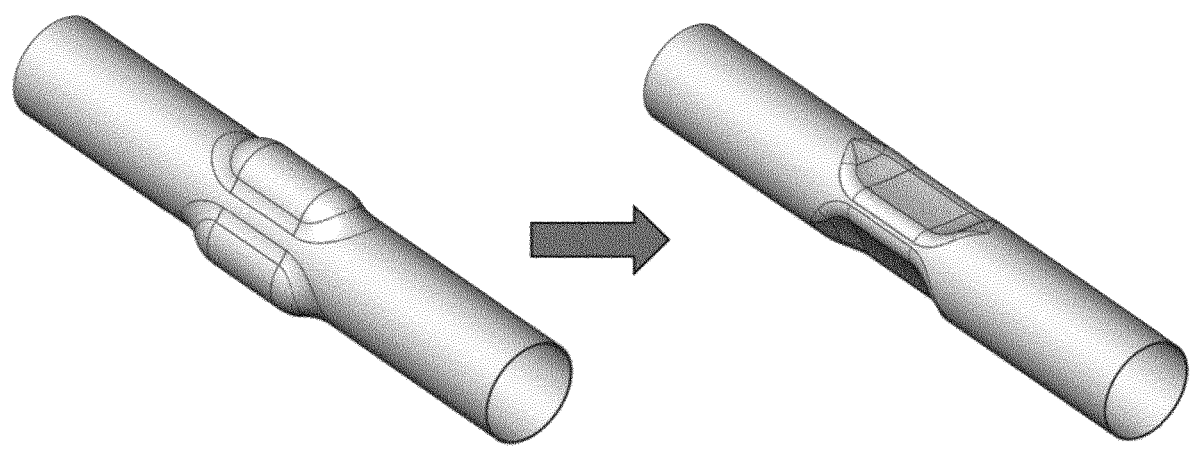
Figure 10A:
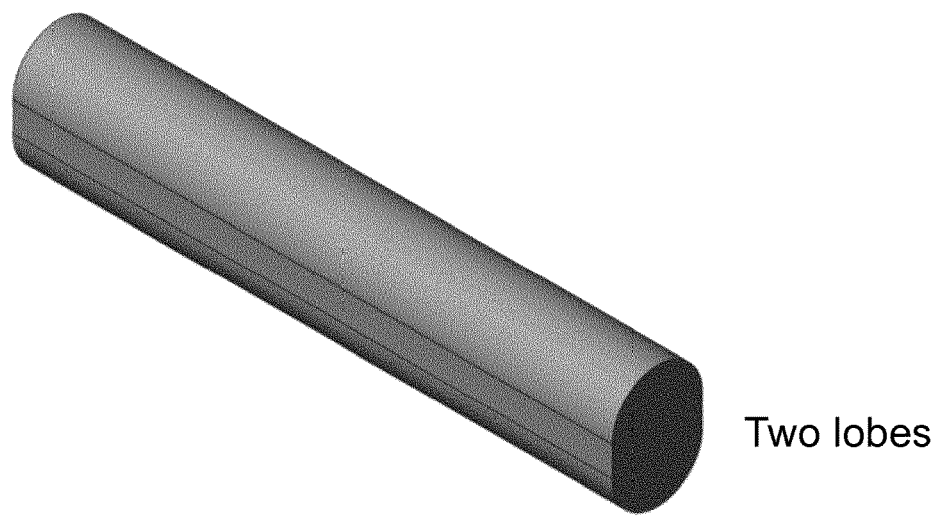
FIGS. 10A-C show according to an exemplary embodiment of the invention in FIG. 10A a mandrel which is used to create the preform shown in FIG. 10B (left).
Figure 10B:
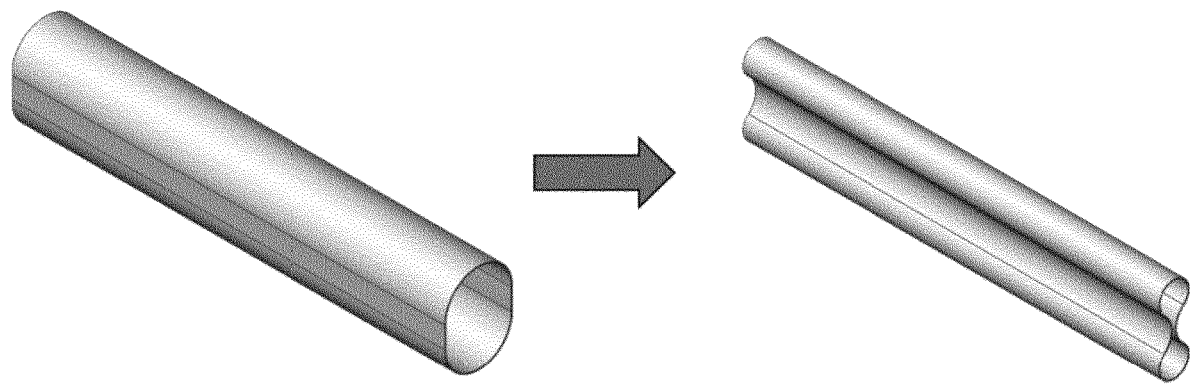
Figure 10C:
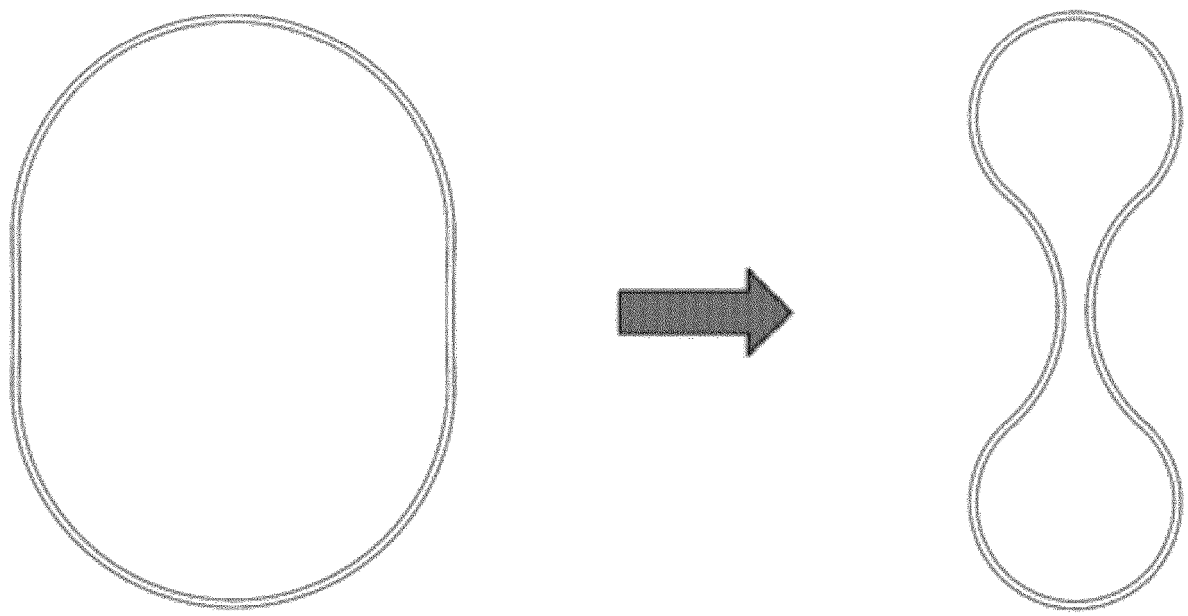
Figure 11A:
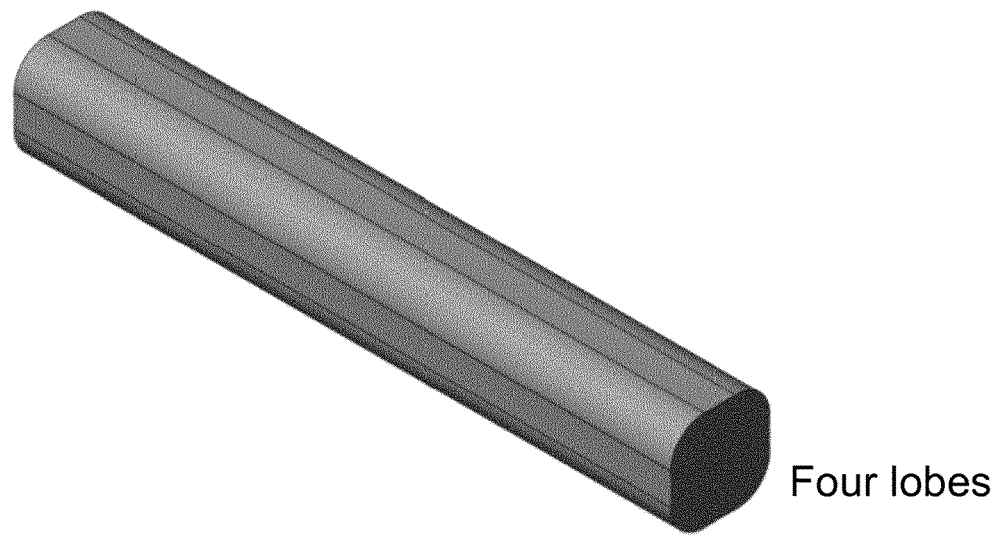
FIGS. 11A-C show according to an exemplary embodiment of the invention in FIG. 11A a mandrel which is used to create the preform shown in FIG. 11B (left).
Figure 11B:
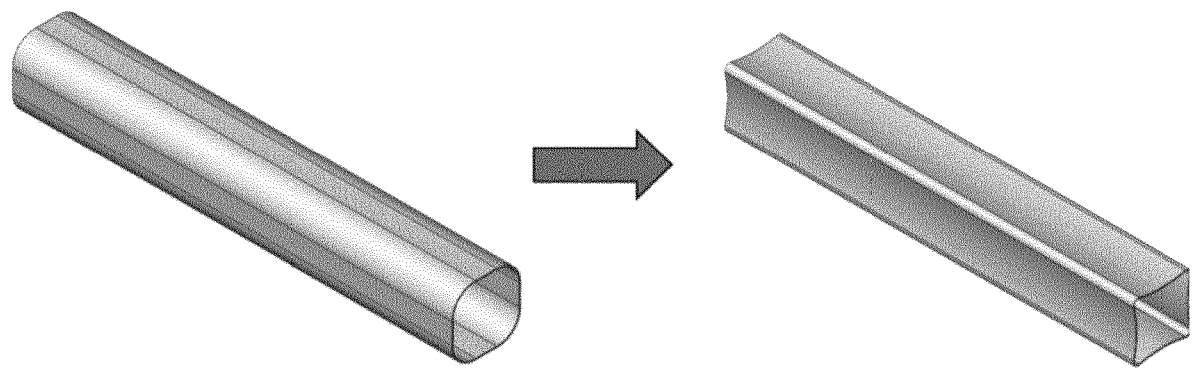
Figure 11C:
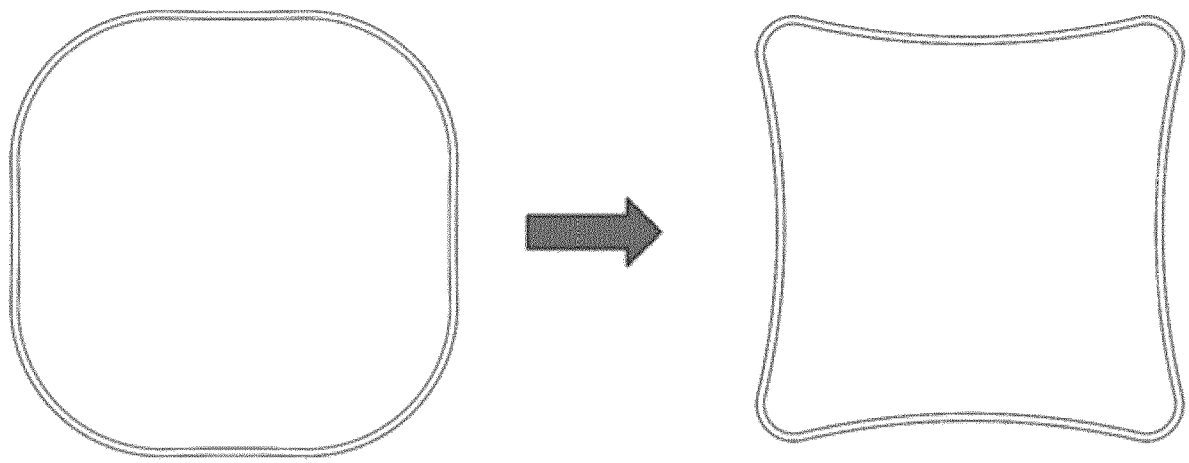
Figure 12A:
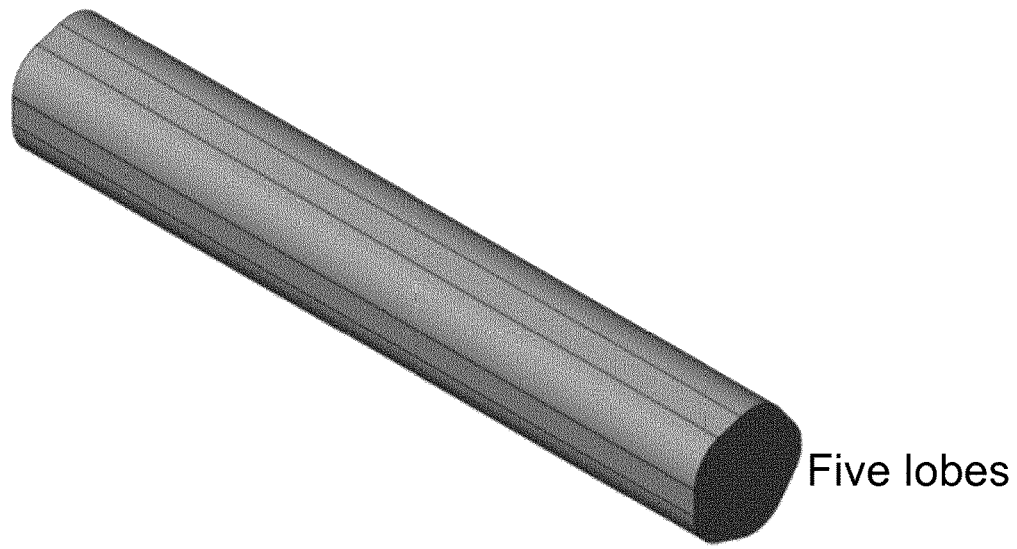
FIGS. 12A-C show according to an exemplary embodiment of the invention in FIG. 12A a mandrel which is used to create the preform shown in FIG. 12B (left).
Figure 12B:
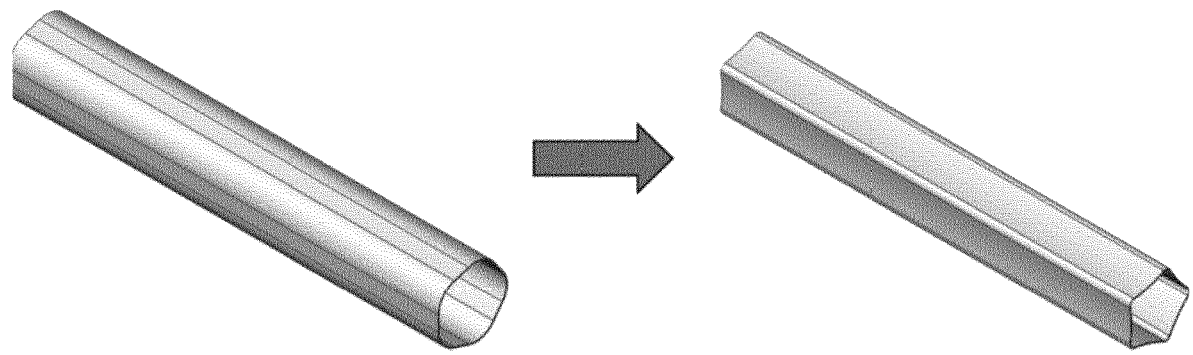
Figure 12C:
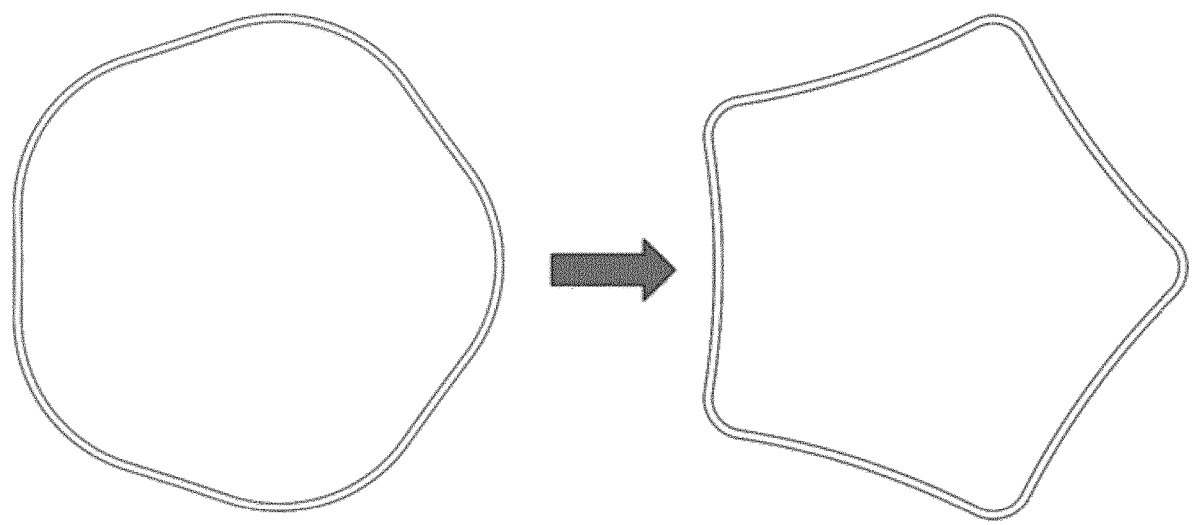

In the example of FIGS. 9A-B, the mandrel shown in FIG. 9A distinguishes a complex shape with mainly convex shapes and only very limited concave areas. In this example, the mandrel and the resulting preform distinguishes a complex shape with mainly convex shapes and only very local concave areas. In this example, the mandrel has local lobes attached to the cylindrical base. These lobed sections have mainly convex shapes and only very limited concave areas. FIG. 9B (left) is the preform that is formed using the mandrel (FIG. 9A). FIG. 9B (right) is the preform after the preform in FIG. 9B (left) is flipped inside-out. The resulting tubular preforms and the final preform (after flipping inside-out) could be advantageous in cases where a section of the preform has to conform to a specific shape, e.g. the indented section can be used to form the leaflets of a heart valve.

Additional Examples

The method of the invention is applicable for targets with two or more lobes. As shown in FIGS. 9A-B, 10A-B (two lobes) and 11A-B (four lobes) creating a preform with multiple lobes can be applied for transcatheter applications. The lobes create preferential folding lines which allow for a more predictable behaviour of the preform while being crimped.

What is claimed is:

1. A method of making a medical implant, comprising:
   (a) using a polymer solution to form a preform with a desired thickness around the surface of a mandrel, wherein the mandrel has a plurality of three-dimensional convex shapes, wherein the formed preform distinguishes an inner surface and an outer surface;
   (b) removing the formed preform from the mandrel; and
   (c) flipping the formed preform inside-out resulting in the inner surface of the formed preform becoming the outer surface of the inside-out flipped preform, and the outer surface of the formed preform becoming the inner surface of the inside-out flipped preform, wherein at least part of the inside-out flipped preform forms the medical implant with a plurality of three-dimensional concave shapes;
   (d) maintaining the concave shapes of the plurality of three-dimensional concave shapes as the medical implant.

2. The method as set forth in claim 1, wherein the step of forming the preform on the mandrel comprises electrospinning the polymer solution on the mandrel.

3. The method as set forth in claim 1, wherein the medical implant is an artificial heart valve, an artificial leaflet, an artificial graft, or an artificial vessel.

* * * * *